(12) United States Patent
Boehm-Van Diggelen (10) Patent No.: US 8,449,297 B2
(45) Date of Patent: May 28, 2013

(54) DENTAL IMPLANT FOR INSERTION INTO A JAWBONE AND FOR FASTENING A TOOTH REPLACEMENT

(76) Inventor: Bernd Boehm-Van Diggelen, Nuremberg (DE)

( * ) Notice: Subject to any disclaimer, the term of this patent is extended or adjusted under 35 U.S.C. 154(b) by 0 days.

(21) Appl. No.: 13/126,307

(22) PCT Filed: Nov. 2, 2009

(86) PCT No.: PCT/DE2009/001527
§ 371 (c)(1),
(2), (4) Date: Apr. 27, 2011

(87) PCT Pub. No.: WO2010/048944
PCT Pub. Date: May 6, 2010

(65) Prior Publication Data
US 2011/0207083 A1    Aug. 25, 2011

(30) Foreign Application Priority Data
Oct. 31, 2008 (DE) .................. 10 2008 054 186

(51) Int. Cl.
*A61C 8/00* (2006.01)
(52) U.S. Cl.
USPC .......................................... 433/173
(58) Field of Classification Search
USPC .......................... 433/173, 174, 175
See application file for complete search history.

(56) References Cited

U.S. PATENT DOCUMENTS

| | | | | |
|---|---|---|---|---|
| 3,579,831 A * | 5/1971 | Stevens et al. | ............. | 433/174 |
| 3,955,280 A * | 5/1976 | Sneer | .............. | 433/169 |
| 4,279,598 A * | 7/1981 | Scheicher | .............. | 433/173 |
| 4,531,916 A * | 7/1985 | Scantlebury et al. | ........ | 433/173 |
| 5,074,790 A * | 12/1991 | Bauer | .............. | 433/174 |
| 5,219,287 A * | 6/1993 | Nishihara | .......... | 433/201.1 |
| 5,246,370 A * | 9/1993 | Coatoam | .............. | 433/173 |
| 5,302,127 A * | 4/1994 | Crisio, Jr. | .............. | 433/173 |
| 5,984,681 A * | 11/1999 | Huang | .............. | 433/174 |
| 6,854,972 B1 * | 2/2005 | Elian | .............. | 433/173 |
| 7,179,088 B2 * | 2/2007 | Schulter et al. | .......... | 433/173 |
| 7,303,396 B2 * | 12/2007 | Abarno | .............. | 433/173 |
| 2006/0154203 A1 * | 7/2006 | Emanuelli | .......... | 433/173 |
| 2010/0055646 A1 * | 3/2010 | Zhao | .............. | 433/174 |
| 2010/0330530 A1 * | 12/2010 | Menzel et al. | .......... | 433/173 |
| 2011/0207083 A1 * | 8/2011 | Boehm-Van Diggelen | .. | 433/173 |

FOREIGN PATENT DOCUMENTS

| | | |
|---|---|---|
| CN | 101 530 350 A | 9/2009 |
| DE | 197 53 577 A1 | 6/1999 |
| DE | 198 28 018 A1 | 12/1999 |
| DE | 10 2006 053 260 A1 | 1/2008 |
| WO | 2008 125049 A1 | 10/2008 |
| WO | 2008 125097 A1 | 10/2008 |

\* cited by examiner

*Primary Examiner* — Ralph Lewis
(74) *Attorney, Agent, or Firm* — Lucas & Mercanti, LLP

(57) ABSTRACT

A dental implant inserted into a jawbone in order to fasten a tooth replacement is characterized by a shape corresponding to two partially overlapping cylinder-like members (29, 30) that have significantly different diameters. The axis of symmetry (14) of the first member (29) having the larger diameter extends perpendicular to the cortical bone (4) of the jawbone, while the axis of symmetry (15) of the second member (30) having the smaller diameter is tilted by an acute angle relative to the axis of symmetry (14) of the first member (29). The point of intersection (2) between the axes of symmetry (14, 15) lies on the axis of symmetry of the first member (29), within or outside said member (29).

12 Claims, 6 Drawing Sheets

DENTAL IMPLANT FOR INSERTION INTO A JAWBONE AND FOR FASTENING A TOOTH REPLACEMENT

CROSS REFERENCE TO RELATED APPLICATIONS

This application is a 371 of PCT/DE2009/001527 filed Nov. 2, 2009, which in turn claims the priority of DE 10 2008 054 186.9 filed Oct. 31, 2008, the priority of both applications is hereby claimed and both applications are incorporated by reference herein.

BACKGROUND OF THE INVENTION

The invention relates to a dental implant for insertion into a jawbone and for fastening a tooth replacement.

A great many dental implants are known, of which the implant known from DE 10 2006 053 260 A1 will serve as an example, which implant, like most other known implants, is provided with a thread on its conical outer surface. With this thread, which is often self-tapping, the implant is screwed with force into a hole formed in the jawbone, where it remains for some time in order to become incorporated, until such time as it can be established that the process of incorporation has been successfully completed.

Most implant failures occur in the critical early phase of incorporation between the second and fourth weeks. At this stage there is a break in terms of stability, caused by a decline of the primary stability and by the increase in secondary stability started by the process of incorporation.

In the known implants, it is regarded as imperative to achieve a high degree of primary stability. This is to be understood as meaning that the implant, after insertion, is connected as firmly as possible to the bone. This is permitted, on the one hand, by the implant having the greatest possible contact with the bone, and, on the other hand, by the bone that surrounds the implant being as firm as possible. This is based on the idea that a high degree of primary stability also promises at a later stage a higher degree of secondary stability, and on the idea too that the implant can be subjected as soon as possible to loads.

The measures proposed for this purpose in terms of macrostructure entail either a compaction of the bone prior to insertion of the implant, for example by a bone expansion screw and/or by the use of a screw implant, in which case the bone is also compacted by the thread among other things.

The known screw implants have the disadvantage that a compaction of the bone represents bone compression, that is to say crushing. This appears to ignore the fact that the forces acting on the implant cause iatrogenic damage, which necessarily lengthens the healing time, because the crushed spongy substance and the compact substance first have to be degraded and then built up again. The crushing of the bone also increases the risk of a gap generally forming around the implant, which also fails to withstand a rotational load.

After the period of incorporation is completed, the implant has to be exposed in a further intervention. For this purpose, the mucosa across the implant is cut open under local anesthesia and a gingiva shaper (a small titanium coping) is screwed onto the implant. This gingiva shaper then protrudes through the mucosa which, over the following weeks, attaches itself to the gingiva shaper and heals. After about one to two weeks the gingiva shaper is temporarily replaced by a special impression coping specifically adapted to the implant, which impression coping is designed to permit an absolutely exact impression of the implant for the production of the tooth replacement. After the impression has been taken, the gingiva shaper is again fastened on the implant to ensure that the shape of the gum does not change. When the tooth replacement is ready, the gingiva shaper is unscrewed again from the implant and replaced by an abutment (titanium post), which remains permanently in the mouth for the purpose of fastening the tooth replacement.

This known method has the disadvantage that, after the period of incorporation, the mucosa across the implant has to be cut open in order to apply a gingiva shaper there, and this requires further local anesthesia and a further healing time for the new wound.

A further disadvantage is the use of an impression coping which, in exchange for the gingiva shaper, has to be screwed onto the implant for taking the impression and which, after the impression has been taken, is replaced again by the gingiva shaper in order to ensure that the shape of the gingiva does not change during the waiting period before the final tooth replacement is finished.

SUMMARY OF THE INVENTION

It is an object of the invention to improve an implant in such a way that it can be quickly and easily inserted, particularly also in a manner secure against rotation, and such that the implant as quickly as possible undergoes osseointegration, i.e. a direct structural union, visible under light microscopy, between the organized vital bone tissue and the surface of the implant.

A further object is to ensure that the impression can be taken as easily and as quickly as possible, and without causing injury, such that the risk of infection is minimized.

A third object is to reduce the amount of work involved in alternately screwing and unscrewing the gingiva shaper, impression coping and abutment before and after the impression is taken.

The first object is achieved by a shape corresponding to two partially overlapping cylinder-like bodies that have significantly different diameters, wherein the axis of symmetry of the first body having the larger diameter extends perpendicular to the compact substance of the jawbone, and the axis of symmetry of the second body having the smaller diameter is tilted at an acute angle relative to the axis of symmetry of the first body, and the point of intersection of the axes of symmetry lies on the axis of symmetry of the first body within or below said body.

The second object is achieved by prior to insertion, a gingiva shaper can be fastened on the head end of the implant with a screw engaging in an internal thread, which gingiva shaper has an internal thread for a further screw with which, after the gingiva surrounding the gingiva shaper has healed and after osseointegration has taken place, an impression coping can be fastened on the gingiva shaper and an impression for the tooth replacement can be taken with an open tray, in that, after the impression material has hardened, and with the gingiva shaper remaining on the implant, the screw of the impression coping can be removed again from the gingiva shaper, and the impression coping, together with the tray, can be lifted from the gingiva shaper, and in that. after the tooth replacement has been finished, the gingiva shaper can also be unscrewed by loosening the screw and can be replaced by an abutment on which, finally, the tooth replacement can be fastened.

The third object is achieved by abutment that is formed integrally on the head end of the implant and, prior to insertion, receives an annular gingiva shaper, the upper edge of which is preferably flush with the upper edge of the abutment and which, after insertion, can be removed again after the gingiva surrounding the gingiva shaper has healed and after osseointegration has taken place, wherein an impression of the abutment can be taken directly with a closed tray and, after the impression material has hardened, the tray can be lifted off and, finally, the finished tooth replacement can be fastened on the abutment.

Advantageous embodiments of the invention are set forth in the following paragraphs.

The first cylinder-like body and/or the second cylinder-like body have a slightly conical shape, with the diameters increasing in the direction of the head end.

An abutment that is formed integrally on the head end of the implant and, prior to insertion, receives an annular gingiva shaper, the upper edge of which is preferably flush with the upper edge of the abutment and which, after insertion, can be removed again after the gingiva surrounding the gingiva shaper has healed and after osseointegration has taken place, and can be replaced by a gingiva shaper with an integrally formed impression coping, from which, with a closed tray, an impression can be taken for the tooth replacement, and wherein, after the impression material has hardened, the tray, together with the gingiva shaper with integrally formed impression coping, can be lifted off from the abutment and replaced by the original annular gingiva shaper which, after the tooth replacement has been finished, can be removed again to allow the tooth replacement, finally, to be fastened on the abutment.

At least one locking pin is arranged at the head end of the implant and engages in a corresponding recess on the underside of the gingiva shaper or of the abutment, and at least one further locking pin is arranged on the underside of the impression coping and engages in a corresponding recess on the top of the gingiva shaper.

A circumferential bevel is arranged on the edge of the head end of the implant and engages in a correspondingly protruding edge on the underside of the gingiva shaper or of the abutment.

The endosseous surface area, at least in the area bearing on the compact substance, has a high polish or shallow grooving, and, in the area bearing on the spongy substance, has a deeper grooving that nowhere exceeds the surface level of the high polish or of the shallow grooving.

At least the endosseous surface area is coated with a layer of polytetrafluoroethylene (PTFE).

A hole can be formed in the jawbone using a drill with a diameter corresponding to the larger diameter of the first cylinder-like body, in that a measuring gauge can be applied to the hole and markings can be made on the jawbone, and in that the hole can be widened in the desired directions as far as the markings by tilting a drill that has a non-cutting drill head with a diameter corresponding to the smaller diameter of the second cylinder-like body.

A hole can be formed in the jawbone using a conical drill with a shape corresponding to the larger shape of the first slightly conical body, in that a measuring gauge can he applied to the hole and markings can be made on the jawbone, and in that the hole can he widened in the desired directions as far as the markings by tilting a conical drill that has a non-cutting drill head with a shape corresponding to the smaller shape of the second slightly conical body.

The advantages afforded by the invention are in particular that the quick insertion of the implant reduces the operating time and that any hematomas and swelling that occur are less pronounced. Moreover, the conicity of the implant, particularly in the area of the compact substance, minimizes the gap between the implant and the bone, such that no germs can gain entry. Moreover, the rotationally stable shape of the implant and its stability against tilting reliably minimize twisting and tilting of the implant, particularly during the initial period of incorporation, as a result of which the incorporation time is further reduced. Moreover, the coating with polytetrafluoroethylene (PTFE) results in an elastic coating similar to the desmodontium (intermediate layer between tooth and jawbone), which elastic coating permits a movement of the implant under physiological loads, without the implant coming loose.

A further advantage is that the method for taking the impression is simplified, thereby greatly reducing the work involved and the material used before and after the impression is taken and until final implantation of the tooth replacement, since the two screws and the two threads in the implant and in the gingiva shaper are omitted.

An illustrative embodiment of the invention, described in more detail below, is shown in the drawings, in which.

Figure 1:
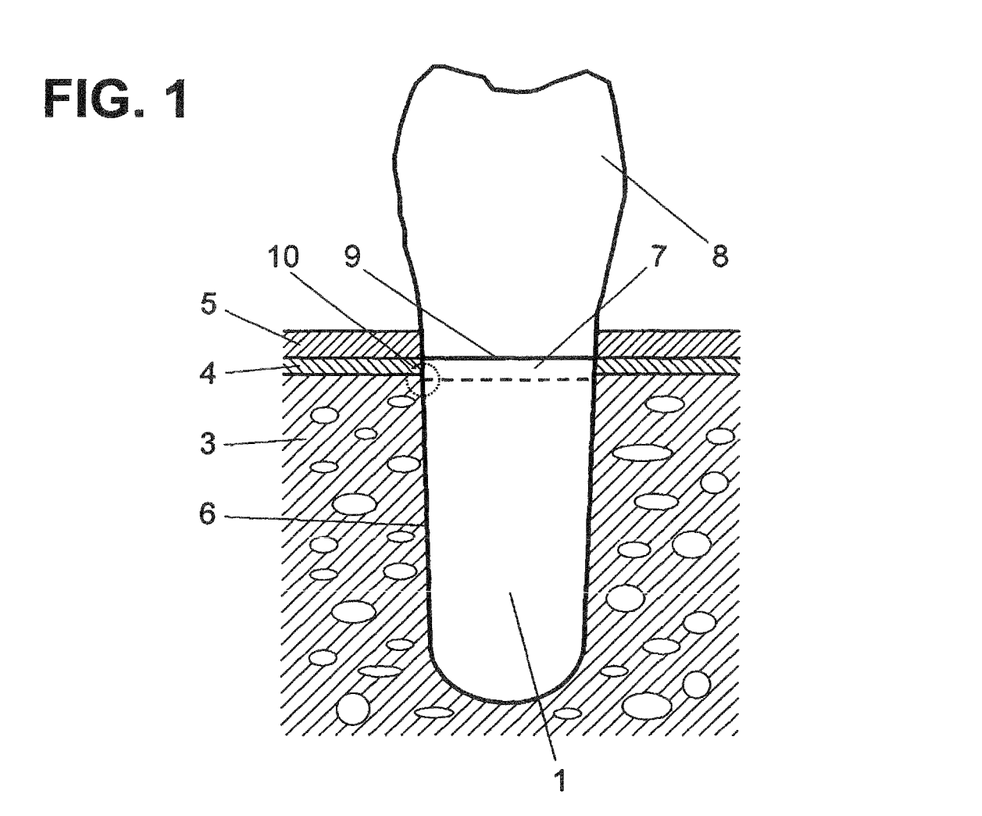
FIG. 1 shows a dental implant with a tooth replacement in a recess of a jawbone and also shows an enlarged detail (1*a*) of the transition from the shallow grooving to the deeper grooving in the surface of the implant.

The dental implant 1 according to the invention in FIG. 1 has a slightly conical shape and is inserted into a corresponding recess formed in a jawbone.

Figure 1A:
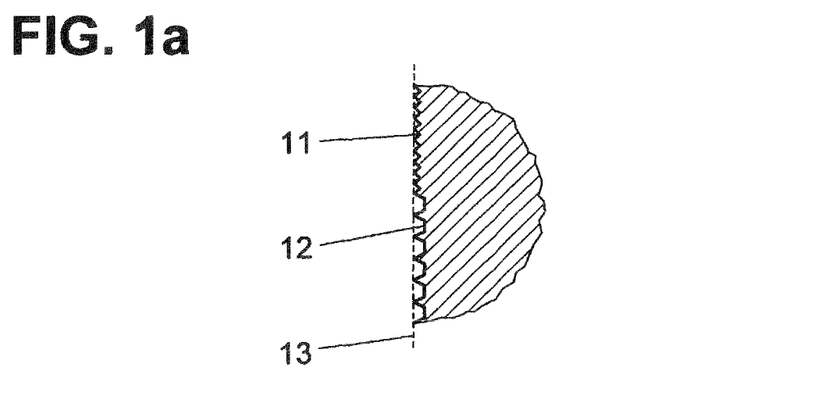

The endosseous area 6, 7 of the surface of the implant 1 (the area engaging in the jawbone) has a shallow grooving 11, at least in the area 7 bearing on the compact substance 4 (hard outer layer of bone), while a deeper grooving 12 is formed in the area 6 bearing on the spongy substance 3 (fine trabecular network in the interior of the jawbone), which deeper grooving 12 nowhere exceeds the surface level 13 of the shallow grooving 11, as is shown in FIG. 1*a*.

This is achieved by a suitable production method in which the surface of the implant 1 is first machined in the endosseous area 6, 7, in order thereafter to provide the area 7 bearing on the compact substance 4 with a shallow grooving and to provide the area 6 bearing on the spongy substance 3 with a deeper grooving 12. This sequence of machining has the effect that the high peaks and valleys 12 occurring on the metal surface nowhere exceed the small peaks and valleys 11, as is indicated by the broken line 13 in the schematic view in FIG. 1*a*. This avoids a situation where, after insertion of such an implant, a gap forms between the compact substance 4 and the neck provided with the shallow grooving.

This technique, in combination with a conical implant shape, represents an excellent measure for reducing the risk of peri-implantitis and for reducing the time needed for incorporation.

A major problem of the known dental implants is the circular cross section which, in contrast to a natural root shape, cannot prevent a rotation.

Figure 2:
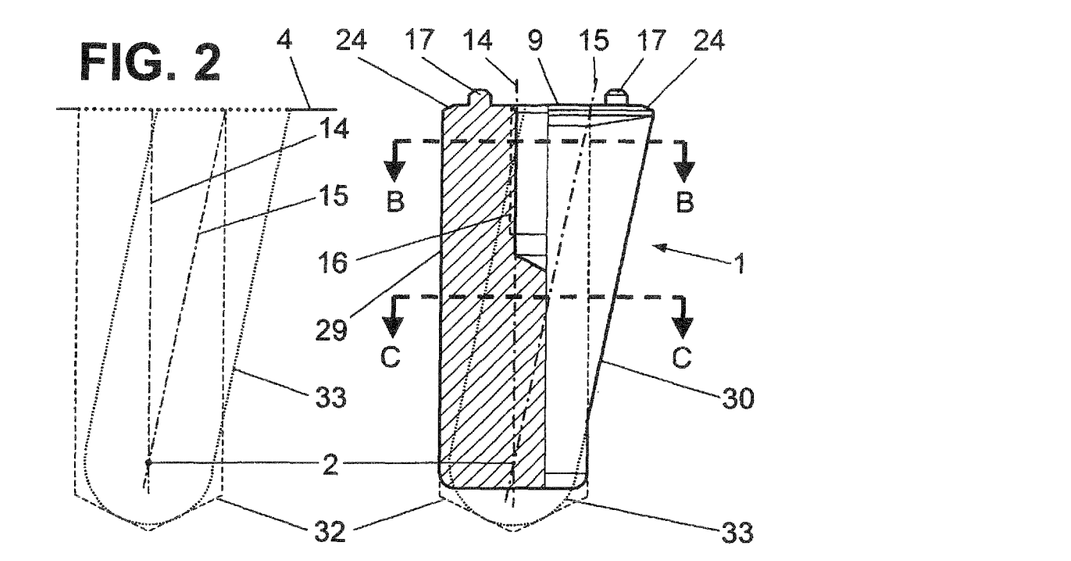
FIG. 2 shows a view of an implant, partially in section, and also a view from above (2*a*), a section B-B (2*b*), and a section C-C (2*c*)

This problem is solved by the anatomically designed implant according to FIG. 2, which has a shape corresponding to two partially overlapping cylinder-like bodies 29, 30 that have significantly different diameters. In the state of insertion in the jawbone, the axis of symmetry 14 of the first body 29 having the larger diameter extends perpendicular to the compact substance 4, and the axis of symmetry 15 of the second body 30 having the smaller diameter is tilted at an acute angle relative to the axis of symmetry 14 of the first body 29. The point of intersection 2 of the axes of symmetry 14, 15 lies on the axis of symmetry of the first body 29, specifically in the lower area thereof.

Figures 2A, 2B:
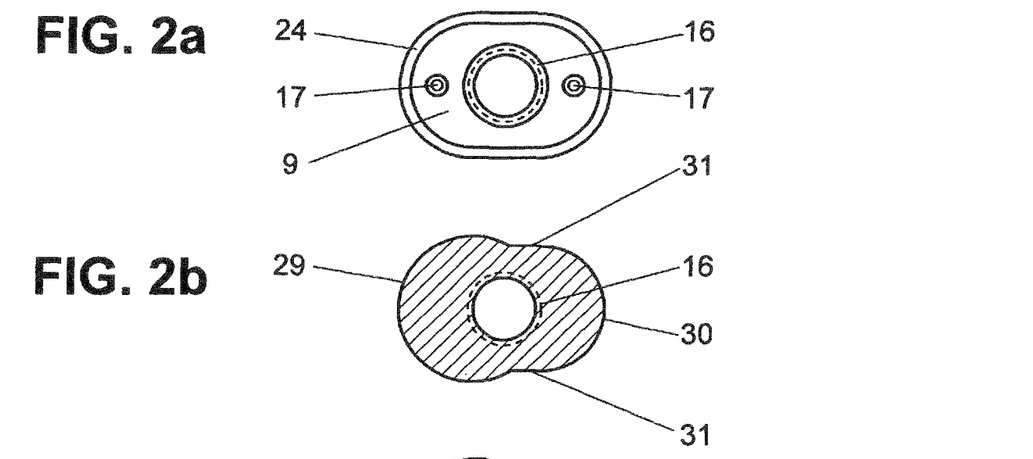

FIG. 2a shows a view of the implant from above, where the thread 16, the locking pins 17 and the circumferential bevel 24 can clearly be seen.

FIG. 2b shows the section B-B, in which the different diameters of the two overlapping cylinder-like bodies 29, 30 can be seen, and also the lateral connecting surfaces 31 between the two bodies 29, 30.

Figure 2C:
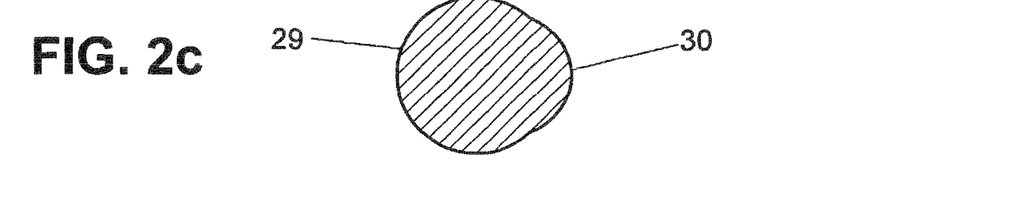

FIG. 2c shows the section C-C. In this area there is a significant overlapping of the bodies 29, 30, and this overlapping further increases in the downward direction, as can also be seen clearly from FIG. 2.

The recess that has to be made in the jawbone for this implant 1 can be produced by simple drilling with the aid of a measuring gauge, by means of the drill being tilted inside the measuring gauge. In FIG. 2, on the left, the perpendicular recess 32 is indicated by the dashed lines, and the recess 33 achieved by the tilted smaller drill is indicated by the dotted lines. The smaller tilted drill has the effect that, even with an imprecise tilting during drilling, the implant cannot tilt, since it is secured in all directions by the first, perpendicular recess 32 having the larger diameter.

Figure 3:
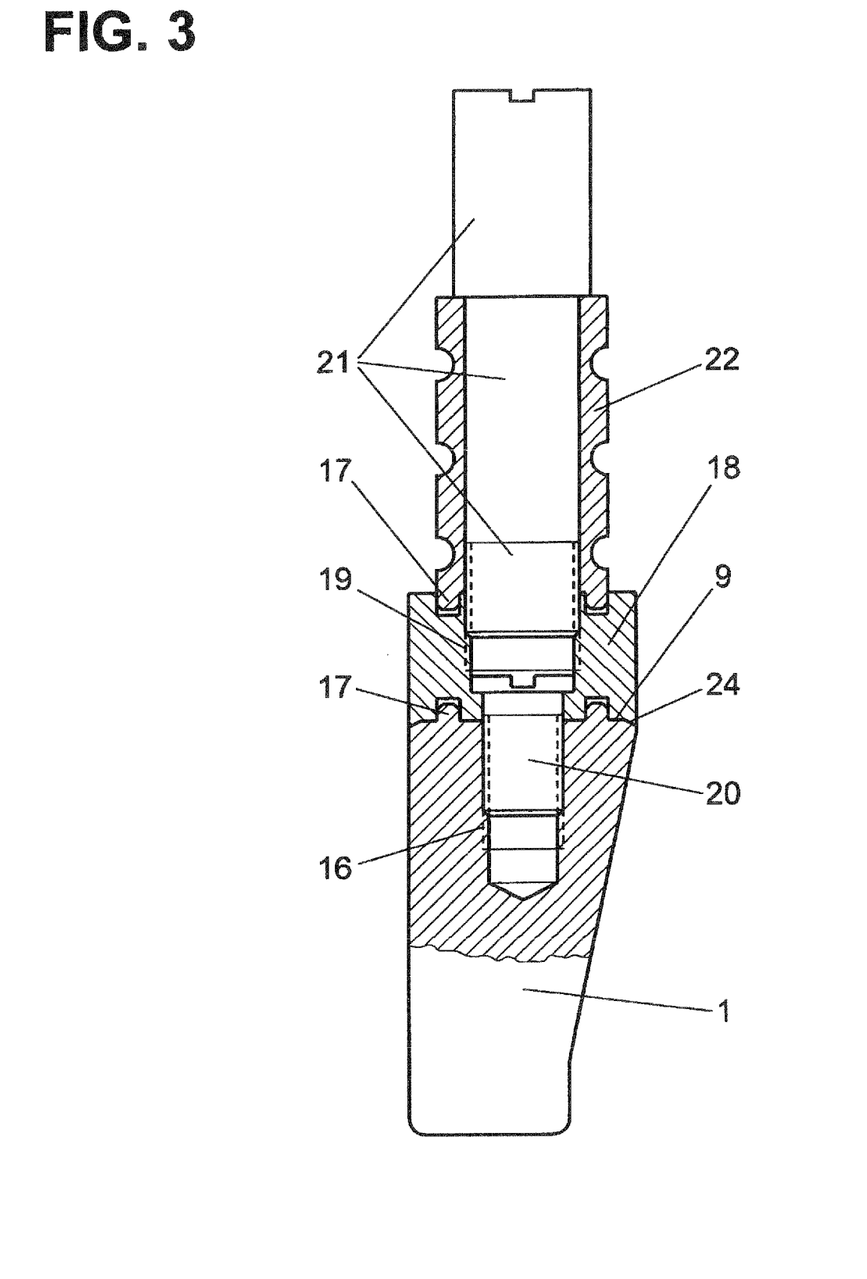
FIG. 3 shows an implant with a gingiva shaper screwed on and with an impression coping screwed on, partially in section.

FIG. 3 shows an implant 1 for insertion into a jawbone, which implant 1 has an internal thread 16 by which, prior to insertion, a gingiva shaper 18 is secured with a screw 20 on the head end 9 of the implant 1. The gingiva shaper 18 likewise has an internal thread 19 for a further screw 21 with which, after the gingiva 5 surrounding the gingiva shaper 18 has healed and after osseointegration has taken place, an impression coping 22 is screwed on for taking an impression for the tooth replacement 8.

After the impression material located on an open tray has hardened, the impression coping 22 is removed again from the gingiva shaper 18 by undoing the screw 21, and the tray is taken off again, while the gingiva shaper 18 remains on the implant 1 in order to maintain the shape of the gingiva 5.

Figure 4:
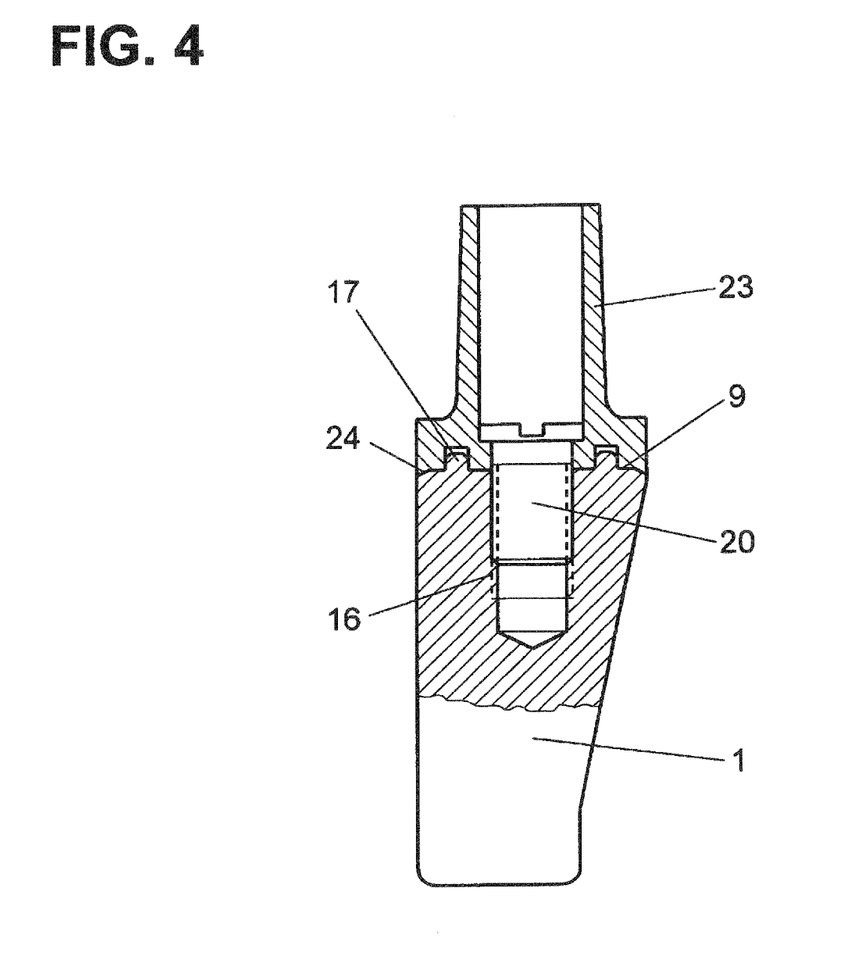
FIG. 4 shows an implant with an abutment screwed on, partially in section.

Only after the tooth replacement 8 has been finished is the gingiva shaper 18 released, by undoing the screw 20, and replaced by an abutment 23, which is screwed securely on the implant 1 using the screw 20, as is shown in FIG. 4. The tooth replacement 8 is then finally fastened on the abutment 23.

This procedure avoids a situation where the impression coping 22 for taking the impression has to be screwed in exchange for the gingiva shaper 18 onto the implant 1, in order to be replaced by the gingiva shaper 18 after the impression has been taken, so as to maintain the shape of the gingiva 18, and in order to unscrew the gingiva shaper 18 again, after the tooth replacement 8 has been finished, and replace it by the abutment 23, which as a whole would entail a great deal of time and work and would increase the risk of injury caused by squeezing the gingiva 5.

Figure 5:
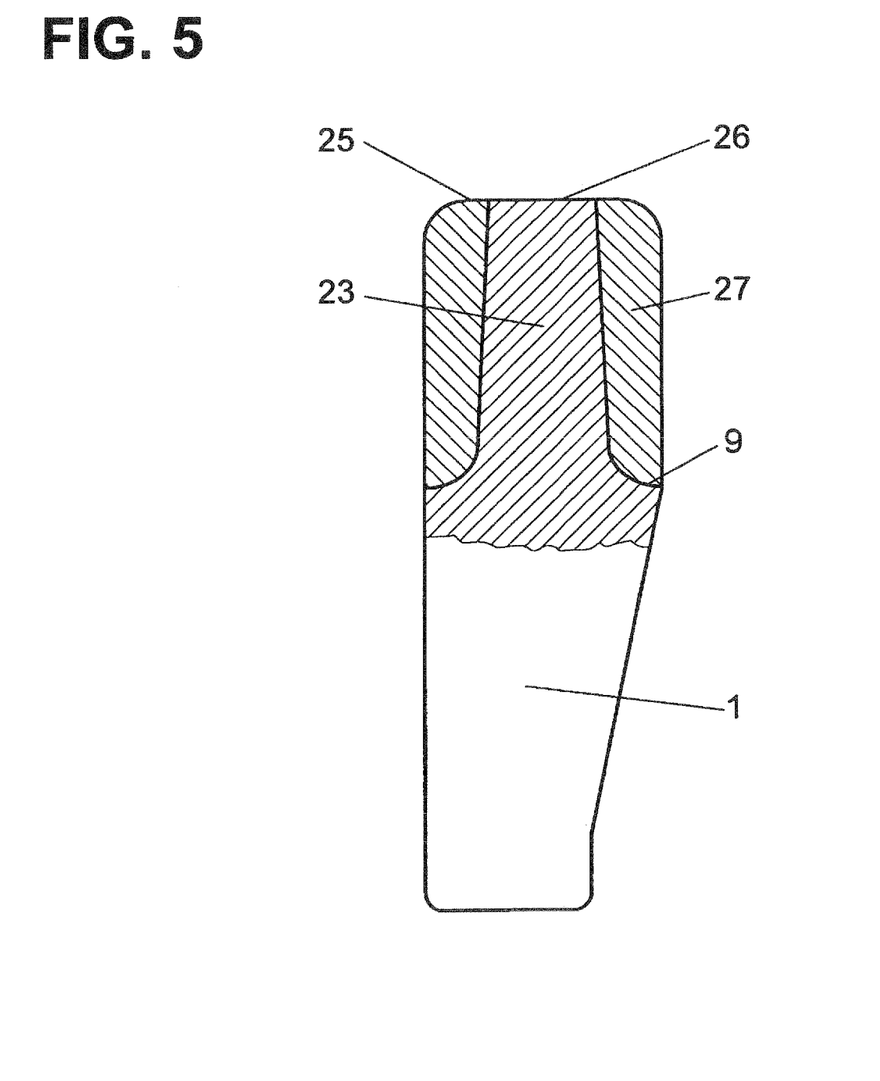
FIG. 5 shows an implant with an integrally formed abutment and with an attached gingiva shaper, partially in section.

FIG. 5 shows an implant 1 having an abutment 23 that is formed integrally on the head end 9 and, prior to insertion, receives an annular gingiva shaper 27, the upper edge 25 of which is preferably flush with the upper edge 26 of the abutment 23. After insertion, and after the gingiva 5 surrounding the gingiva shaper 27 has healed and after osseointegration has taken place, the gingiva shaper 27 is removed, wherein the abutment 23 serves as an impression coping for taking an impression for the tooth replacement 8, and wherein a closed tray can be used. After the impression material has hardened, the tray is removed, and the tooth replacement 8, after it has been finished, is finally fastened on the abutment 23.

Figure 6:
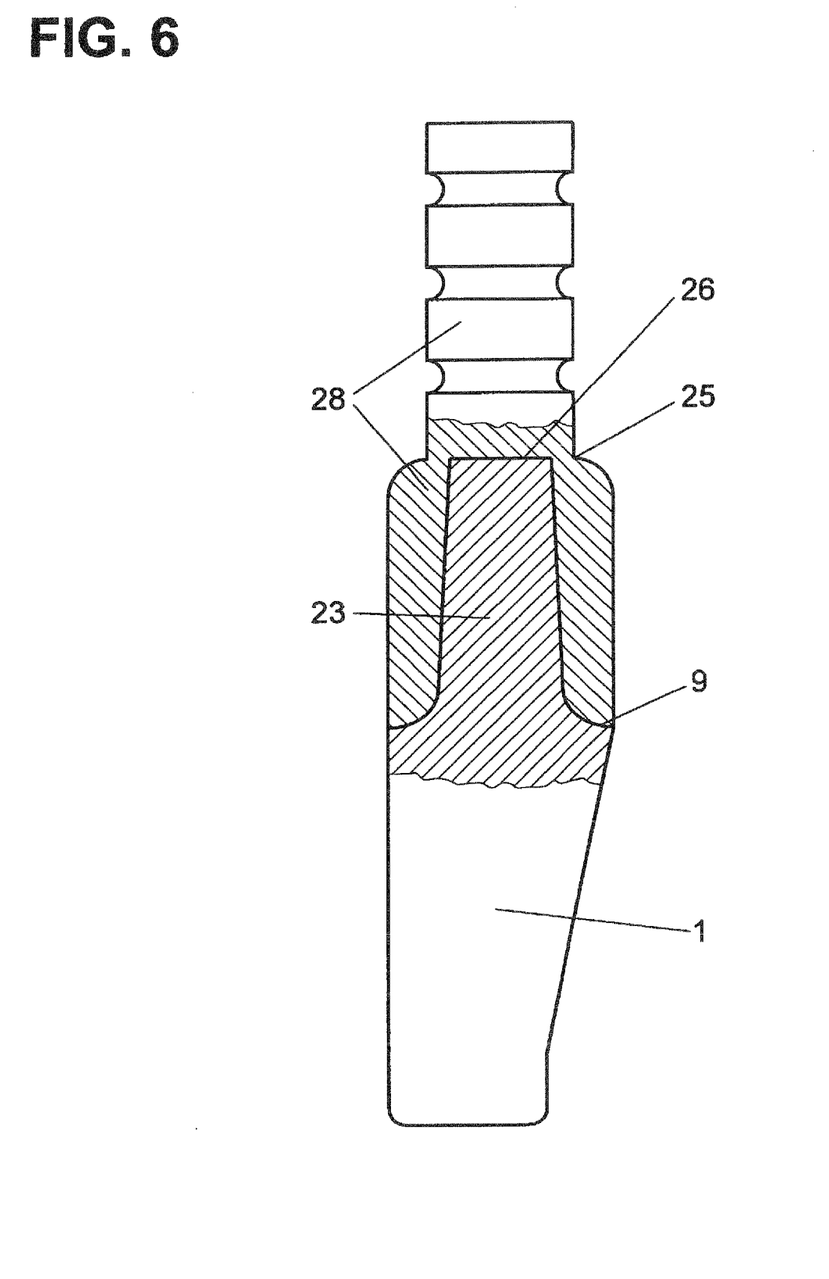
FIG. 6 shows an implant with an integrally formed abutment and with an attached gingiva shaper having an integrally formed impression coping, partially in section.

FIG. 6 shows an implant 1 having an abutment 23 that is formed integrally on the head end 9 and, prior to insertion, receives an annular gingiva shaper 27 (FIG. 5), the upper edge 25 of which is flush with the upper edge 26 of the abutment 23 and which, after insertion, and after the gingiva 5 surrounding the gingiva shaper 27 has healed and after osseointegration has taken place, can be removed again and replaced by a gingiva shaper with an integrally formed impression coping 28, from which, with a closed tray, an impression can be taken for the tooth replacement 8, and wherein, after the impression material has hardened, the tray, together with the gingiva shaper with integrally formed impression coping 28, can be lifted off the abutment 23 and replaced by the annular gingiva shaper 27 which, after the tooth replacement 8 has been finished, can be removed again to allow the tooth replacement 8, finally, to be fastened on the abutment 23.

LIST OF REFERENCE SIGNS 1 implant
2 point of intersection of the axes of symmetry
3 spongy substance
4 compact substance
5 gingiva
6 area bearing on the spongy substance
7 area bearing on the compact substance
8 tooth replacement
9 head end
10 detail for enlargement
11 shallow grooving
12 deeper grooving
13 surface level of the shallow grooving
14 first axis of symmetry
15 second axis of symmetry
16 internal thread of the implant
17 locking pin
18 gingiva shaper
19 internal thread of the gingiva shaper
20 screw for gingiva shaper or abutment
21 screw for impression coping
22 impression coping
23 abutment
24 bevel
25 upper edge of the gingiva shaper
26 upper edge of the abutment
27 annular gingiva shaper
28 gingiva shaper with impression coping
29 first cylinder-like body
30 second cylinder-like body
31 connecting surface
32 large recess
33 small recess

The invention claimed is:

1. A dental implant for insertion into a jawbone for fastening a tooth replacement, comprising:
a one-piece body having two, side-by-side, partially overlapping, substantially cylindrical parts extending downward from a head end past a middle of the implant;
each of the parts having a significantly different diameter;

a first part of the parts having a larger diameter than a second part of the parts;

each of the parts having an axis of symmetry;

the axis of symmetry of the second part tilted at an acute angle relative to the axis of symmetry of the first part and directed towards a bottom of the implant.

2. The implant of claim 1, wherein the first part and the second part having a conical shape with diameters increasing in the direction of a head end of the implant.

3. The implant of claim 1, wherein the one piece body has a endosseous surface area;

the endosseous surface area having a compact substance surface area and a spongy substance surface area;

a high polish on the compact substance surface area; and grooves on the spongy substance surface area, the grooves not exceeding a surface level of the high polish.

4. The implant of claim 3, wherein a layer of polytetrafluoroethylene coats the endosseous surface area.

5. The implant of claim 1, wherein the one piece body has a endosseous surface area;

the endosseous surface area has a compact substance surface area and a spongy substance surface area;

shallow grooves on the compact substance surface area; and deeper grooves on the spongy substance surface area, the deeper grooves being deeper than the shallow grooves, and the deeper grooves not exceeding a surface level of the shallow grooves.

6. The implant of claim 5, wherein a layer of polytetrafluoroethylene coats the endosseous surface area.

7. A method for fastening a tooth replacement on the dental implant of claim 1, comprising:

forming a hole in a jawbone for the implant;

implanting into the hole the implant;

mounting an abutment onto a head end of the implant; and fastening a tooth replacement onto the mounted abutment after the implant has been implanted.

8. The method of claim 7, further comprising:

fastening, prior to implanting the implant in the hole, a gingiva shaper onto a head end of the implant with a screw that engages internal threads in the implant;

fastening, after implanting and after the gingiva surrounding the gingiva shaper has healed and after osseointegration has taken place, an impression coping onto the gingiva shaper, the gingiva shaper having internal threading for a screw surface of the impression coping;

taking an impression for the tooth replacement with an open tray on the fastened impression coping;

removing, after the impression. material has hardened, the impression and the impression coping together with the tray from the gingiva shaper; and removing the gingiva shaper from the implant after removing the impression and the impression coping, followed by mounting the abutment on the implant.

9. The method of claim 8, wherein the head end of the implant has a locking pin which engages a corresponding recess in an underside of the gingiva shaper and a corresponding recess in an underside of the abutment; and an underside of the impression coping has a locking pin which engages a corresponding recess in a top of the gingiva shaper.

10. The method of claim 8, wherein an edge of the head end of the implant has a circumferential bevel that engages a corresponding protruding edge on an underside of the gingiva shaper and the corresponding protruding edge on an underside of the abutment.

11. The method of claim 7, wherein mounting, prior to implanting, the abutment onto the head end of the implant; and further comprising:

mounting, prior to implanting, an annular gingiva shaper onto the mounted abutment;

removing, after implanting and after the gingiva surrounding the annular gingiva shaper has healed and after osseointegration has taken place, the annular gingiva shaper from the abutment;

taking, after removing the annular gingiva shaper, an impression for the tooth replacement with a closed tray directly on the abutment; and removing, after the impression material has hardened, the impression and the closed tray from the abutment followed by fastening the tooth replacement onto the mounted abutment.

12. The method of claim 7, wherein mounting, prior to implanting, the abutment onto the head end of the implant; and further comprising:

mounting, prior to implanting, and annular gingiva shaper onto the mounted abutment;

removing, after implanting and after the gingiva surrounding the annular gingiva shaper has healed and after osseointegration has taken place, the annular gingiva shaper from the abutment;

fastening, after removing the annular gingiva shaper, a gingiva shaper with an integral impression coping onto the abutment;

taking an impression for the tooth replacement with a closed tray on the fastened gingiva shaper with an integral impression coping; and removing, after the impression material has hardened, the impression and the gingiva shaper with an integral impression coping from the abutment, followed by fastening the tooth replacement onto the mounted abutment.

* * * * *